United States Patent
Hoofman et al.

(10) Patent No.: US 8,079,248 B2
(45) Date of Patent: Dec. 20, 2011

(54) MOISTURE SENSOR

(75) Inventors: Romano Hoofman, Geel (BE); Julien Maurice Marcel Michelon, Leuven (BE)

(73) Assignee: NXP B.V., Eindhoven (NL)

( * ) Notice: Subject to any disclaimer, the term of this patent is extended or adjusted under 35 U.S.C. 154(b) by 574 days.

(21) Appl. No.: 12/093,667

(22) PCT Filed: Oct. 24, 2006

(86) PCT No.: PCT/IB2006/053907
§ 371 (c)(1),
(2), (4) Date: May 14, 2008

(87) PCT Pub. No.: WO2007/057794
PCT Pub. Date: May 24, 2007

(65) Prior Publication Data
US 2008/0316673 A1 Dec. 25, 2008

(30) Foreign Application Priority Data
Nov. 17, 2005 (EP) ..................... 05110874

(51) Int. Cl.
*G01N 7/00* (2006.01)
(52) U.S. Cl. ........................................ 73/29.01
(58) Field of Classification Search .............. 73/29.01
See application file for complete search history.

(56) References Cited

U.S. PATENT DOCUMENTS

| | | | |
|---|---|---|---|
| 4,057,823 A | 11/1977 | Burkhardt et al. | |
| 6,690,569 B1 | 2/2004 | Mayer et al. | |
| 7,193,290 B2 * | 3/2007 | Benzel et al. | 257/467 |
| 7,319,235 B2 * | 1/2008 | Happ | 257/2 |
| 7,518,380 B2 * | 4/2009 | Bonne et al. | 324/663 |
| 7,554,134 B2 | 6/2009 | Cummins | |
| 7,799,693 B2 * | 9/2010 | Soda | 438/709 |
| 2004/0040378 A1 | 3/2004 | Chen et al. | |
| 2004/0149032 A1 * | 8/2004 | Sell | 73/304 C |
| 2005/0218465 A1 | 10/2005 | Cummins | |
| 2009/0184724 A1 * | 7/2009 | Bonne et al. | 324/663 |

FOREIGN PATENT DOCUMENTS

| | | |
|---|---|---|
| FR | 2356932 A1 | 1/1978 |
| GB | 2158585 A | 11/1985 |
| JP | 2003-516539 A | 5/2003 |
| JP | 2003-270189 A | 9/2003 |

OTHER PUBLICATIONS

Michelon, J; et al "Impact of Moisture on Porous Low-K Reliability" 2005 IIRW Final Report, Oct. 17, 2005, pp. 35-38.
Michelon, J; et al "Moisture Influence on Porous Low-K Reliability" IEEE Transactions on Device and Materials Reliability, vol. 6, No. 2, Jun. 2006, pp. 169-174.
Tokei, Zs. et al. "Reliability Challenges for Copper Low-k Dielectrics and Copper Diffusion Barriers", Microelectronics Reliability, vol. 45, pp. 1436-1442 (Aug. 2005).
Hoofman R. J. O. M. et al., Challenges in the Implementation of Low-k Dielectrics in the Back-end of Line, Microelectronic Engineering, vol. 80, pp. 337-344 (2005).

* cited by examiner

*Primary Examiner* — Hezron E Williams
*Assistant Examiner* — Rodney T Frank

(57) ABSTRACT

A moisture sensor includes interdigitated first and second electrodes formed in trenches A porous low-k dielectric is provided between the electrodes. The electrodes are of Cu surrounded by a barrier layer to protect the Cu from corrosion. TiN may be used as barrier layer and selectively deposited barrier material such as CoWB, MoWB or NiMoP as barrier layer.

18 Claims, 4 Drawing Sheets

MOISTURE SENSOR

The invention relates to a moisture sensor and to a method of making it.

Existing moisture measurement devices are frequently unable to measure very low moisture levels accurately. Further, existing designs are mostly not scalable, and so they cannot be integrated into integrated circuits of ever decreasing size.

U.S. Pat. No. 4,057,823 describes a moisture sensor integrated into an integrated circuit. A small region of a chip is made porous by anodic etching. The region is oxidised to form porous silicon dioxide and a metal electrode deposited over part of the porous area. The large surface area in the dielectric caused by the porous structure means that ambient moisture diffuses into the dielectric and adsorb onto the silicon dioxide. The capacitance or conductance of the device changes and can be measured.

Unfortunately, this patent dates from 1977 and the process described cannot be readily integrated into modern integrated circuit processing. Nor is the structure easy to use—in the example given in the patent a "60 mil" diameter electrode (about 1.5 mm) gives resistance values of order $10^{10}$ ohm which is difficult to measure. A larger area to decrease the resistance would further increase the already large chip area taken up by the sensor.

Thus, there remains a need for a moisture sensor that can be fabricated in a way readily compatible with today's integrated circuit processing, that may be used either integrated into an integrated circuit or as a discrete device.

According to the invention there is provided a moisture sensor, including first and second conductive electrodes each having at least one element, the elements of the first and second conductive electrodes extending in parallel for a total parallel length of at least 0.3 mm and spaced apart by no more than 1 μm; and porous dielectric having a porosity greater than 10% separating the first and second electrodes. In embodiments, the porosity is greater than 20%, and in particular embodiments the porosity is greater than 30%.

A conventional insulator used in semiconductor processing is silicon dioxide, which has a dielectric constant approximately 4.1. Driven by a need for improved interconnect technology, improved conductive layers have been proposed using copper interconnects and porous low-k organosilicate glass material as insulator. "k" here refers to the dielectric constant.

Such porous low-k materials are commercially available for growth using chemical vapour deposition (CVD) under trade names such as Orion™ from Trikon, BDIIx™ from AMAT and Aurora™ from ASMi. Alternative materials can be deposited by being spun on—such materials include SiLK™ from Dow Chemical and LKD™ from JSR.

A known problem for such porous materials is that they can absorb moisture, especially after full processing (since they tend to become hydrophilic due to processing damage).

The inventors have realised that this property can be used to provide a moisture sensor according to the invention that can readily be integrated into existing integrated circuit processing. In particular the moisture sensor uses processing techniques that are suitable for emerging processing technologies and so the moisture sensor may readily be integrated into advanced devices using these techniques that may be manufactured in the years to come.

In a preferred embodiment, the first and second conductive electrodes are interdigitated combs, the teeth of the combs being the elements extending in total for the parallel length of at least 0.3 mm, the teeth of the first and second conductive elements being spaced from each other at the spacing of no more than 1 μm.

Preferably, the dielectric is a low-k dielectric having a dielectric constant (k) less than 3.0. The dielectric is preferably orthosilicate glass (OSG).

In embodiments, the first and second conductive electrodes may be of copper. Other alternatives exist such as aluminium.

A barrier layer may extend around the conductive electrodes to protect the conductive electrodes from corrosion. The barrier layer may be dielectric or conductive.

The barrier may include a first barrier material on the sides and base of the copper electrodes and second barrier material on the top of the electrodes, the first and second barrier materials being different.

The second barrier material may be a material such as CoWB, WoWP, or NiMoP which can be selectively deposited on copper. If an embodiment without a further dielectric layer of the porous dielectric material is used, the copper lines can also be capped by CVD materials such as SiC or Si3N4, which serve as copper diffusion barrier and protect the copper from corrosion as well.

The first barrier material may be deposited by chemical vapour deposition (CVD) or physical vapour definition (PVD). The first barrier material may be metal, for example, TiN, TaN, WN, or Ru.

The invention also relates to the use of a moisture sensor as described above, by applying an electric field from 0.5 to 1 MV/cm between the first and second electrodes, and measuring the current passing between the first and second electrodes as a measure of the moisture content.

In a further aspect, there is provided a method of manufacturing a moisture sensor, comprising: depositing porous dielectric with a porosity of at least 10%; etching through the porous dielectric to form first and second trenches having an element elements extending in parallel for a parallel length of at least 0.3 mm and spaced apart by no more than 1 μm; and filling the trenches with conductor to form first and second conductive electrodes having elements extending in parallel for a parallel length of at least 0.3 mm and spaced apart by no more than 1 μm.

For a better understanding of the invention, embodiments will now be described, purely by way of example, with reference to the accompanying drawings, in which.

The figures are schematic and not to scale. The same and like components are given the same reference numerals in different Figures.

Figure 1:
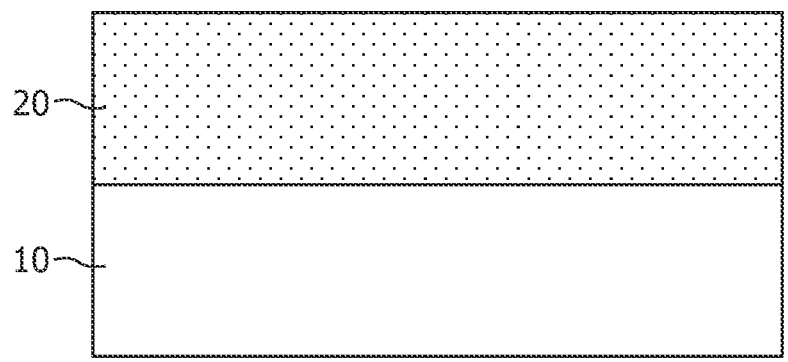
FIGS. 1 to 5 show side sections of steps in a method of manufacturing a moisture sensor according to the invention.

Referring to FIG. 1, a low-k dielectric constant porous organosilicate glass 20 having a dielectric constant (k) approximately 2.7 is deposited on substrate 10. The glass 20 has a porosity greater than 10%. Porosity is defined as the volume of pores divided by the total volume including pores and the material between the pores.

Figure 2:
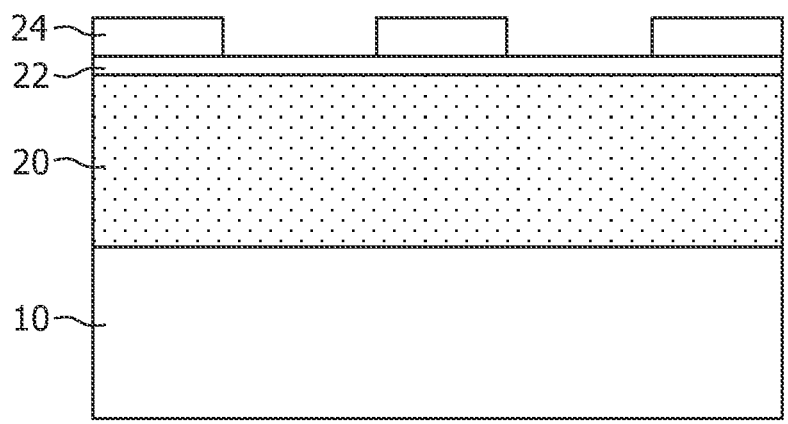

Next, a bottom anti-reflective coating (BARC) layer 22 is deposited, followed by resist 24. The resist 24 is then patterned as illustrated in FIG. 2. The BARC layer improves the photolithographic properties of the resist 24 and is particularly useful in high-resolution photolithography. If it is not required, the BARC layer 22 may be omitted.

Figure 3:
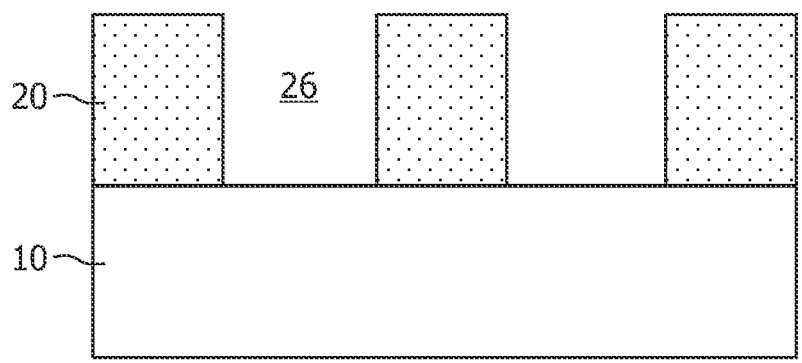

Next, trenches 26 are etched to define an interdigitated comb structure of first and second trenches. The resist 24 and BARC layer 22 are then removed, resulting in the arrangement of FIG. 3.

A barrier layer 28 of a first barrier material is then deposited on the whole surface, covering the sidewalls and base of the trenches 26 as well as the low-k dielectric 20 between the trenches. The shape of the trenches is the same as the shape of the finished electrodes formed in the trenches and will be discussed below with reference to FIG. 6. In the example, the barrier layer 28 is of TiN which is deposited by physical vapour deposition (PVD).

Bulk copper 30 as conductive filling material is then deposited to fill the trenches.

Figure 4:
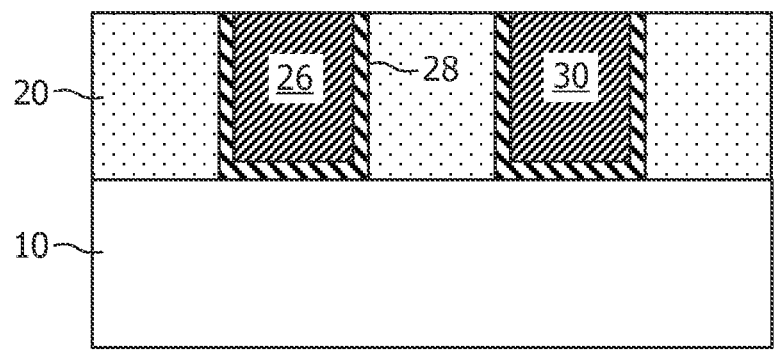

A chemical-mechanical polishing step then removes the top surface including the barrier layer 28 on the surface, any copper on the barrier layer 28 between the trenches 26 as well as the top of the low-k dielectric layer 20, resulting in the structure of FIG. 4.

A further barrier layer 32 of second barrier material is then deposited by a self-aligned process. The second barrier material may be CoWB, CoWP, or NiMoP which can be grown in a self-aligned manner on Cu, to result in the structure of FIG. 5.

The first and second barrier layers 28, 32 thus cooperate to form a barrier around the top, sides and base of the copper 30. This barrier protects the copper from corrosion. The barrier layers 28,32 and copper 30 form electrodes.

Figure 6:
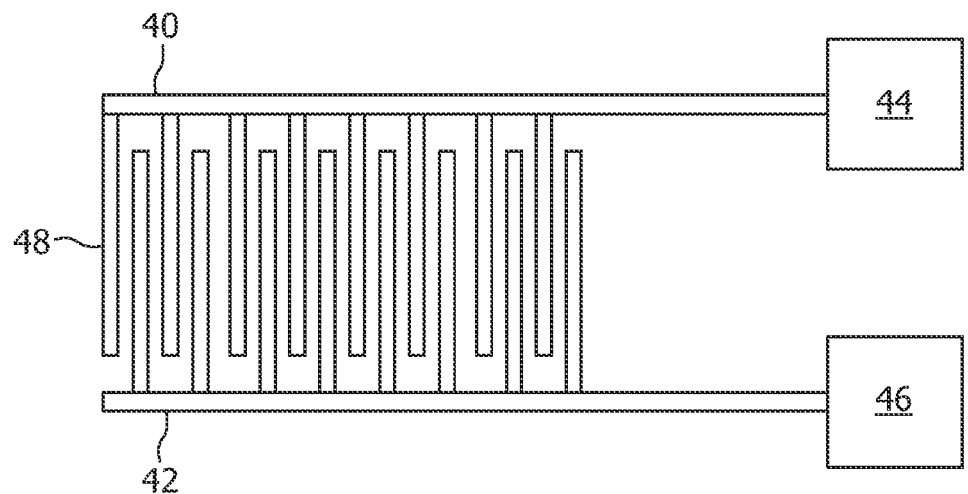
FIG. 6 shows a top view of the moisture sensor of FIG. 5.

A top view of the moisture sensor is provided in FIG. 6 illustrating the interdigitated comb structure of first and second electrodes 40,42 formed of copper. The figure also shows respective first and second bond pads 44, 46. The combs have teeth 48 as elements of the electrodes. As will be appreciated, the electrodes 40, 42 are formed in the trenches 26 and accordingly the trenches 26 have the same structure.

The teeth 48 of the first and second electrodes 40,42 alternate, running in parallel with each other. The total length of teeth 48 of each comb overlapping with the teeth of the other comb exceeds 0.3 mm, and the gap between the teeth 48 laterally of the teeth is less than 1 μm. In this way a large total length can be achieved in a small area.

As will be appreciated by those skilled in the art, the bond pads 44, 46 may themselves be connected to by a further layer of aluminium interconnect and passivation to other devices on the same substrate to integrate the moisture sensor with other devices.

Alternatively, where the device is a discrete device, contacts may be made to the bond pads for example by bonding.

Figure 7:
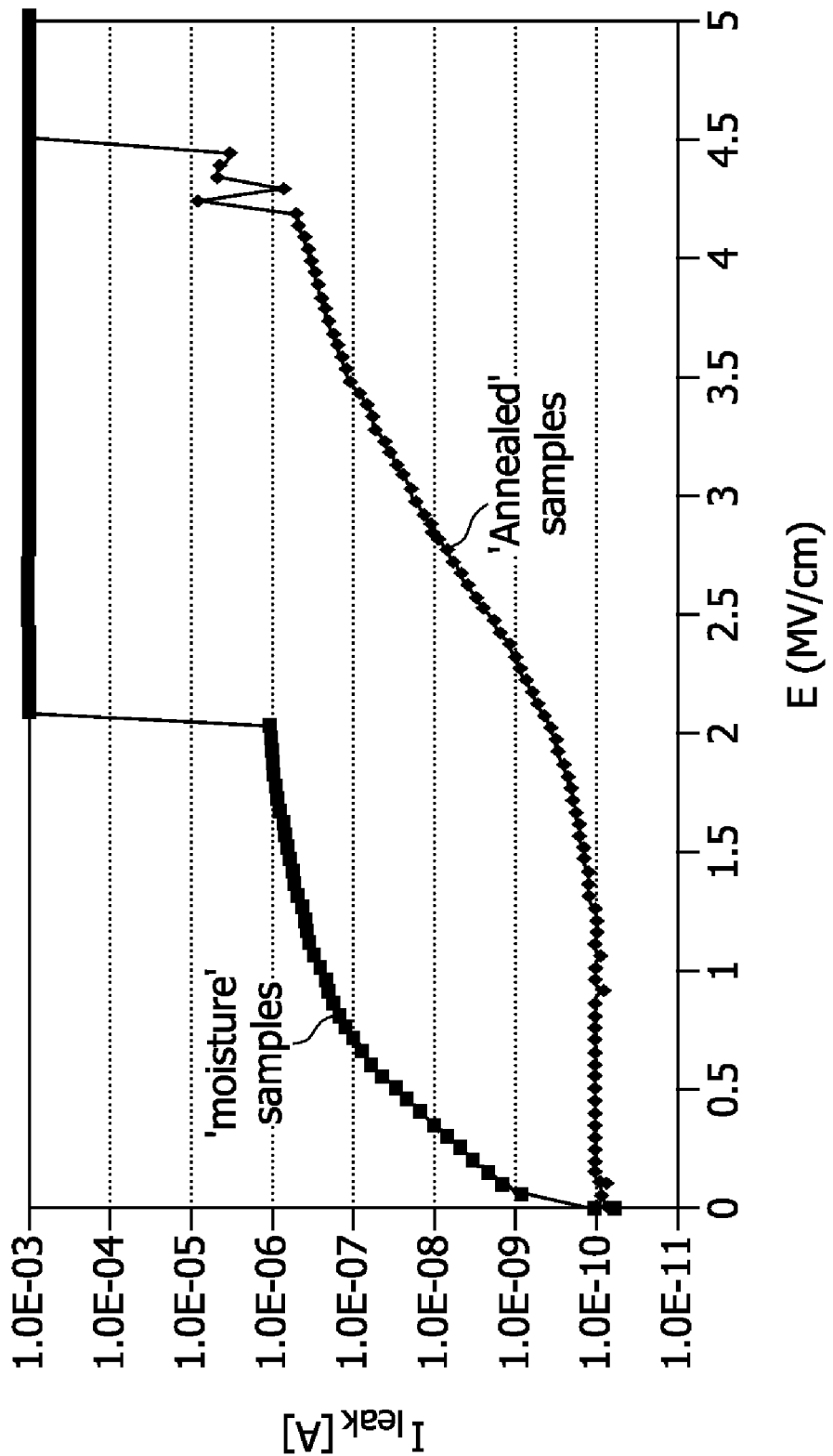
FIG. 7 illustrates measurements made on the moisture sensor of FIGS. 5 and 6.

The current passing between the first and second electrodes 40,42 as a function of the electric field applied between the electrodes is shown in FIG. 7 for two states, one with and one without moisture. The sample without moisture was annealed to ensure that it was completely dry.

The sample used a 40% porosity OSG material with the total length of interdigitated electrodes being 1 cm. The elements of the electrodes were 200 nm apart, i.e. the spacing between the comb parts is 200 nm.

It will be noted that breakdown occurs in the sample with moisture above 2 MV/cm.

Accordingly, in use, a field of 0.5 to 1 MV/cm is applied between the first and second electrodes 40,42 and the current measured. The current is used as a measure of the moisture present—as can be seen in FIG. 7, the current is many orders of magnitude higher in the presence of moisture than without.

Those skilled in the art will realise that alternative processing is possible.

Figure 5:
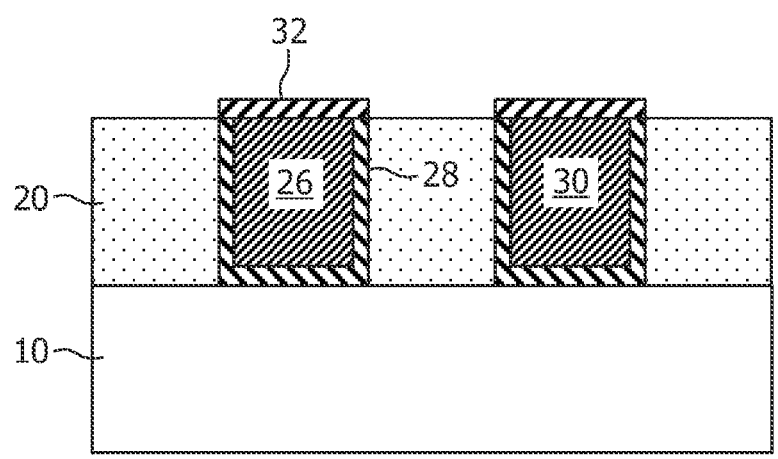
Figure 8:
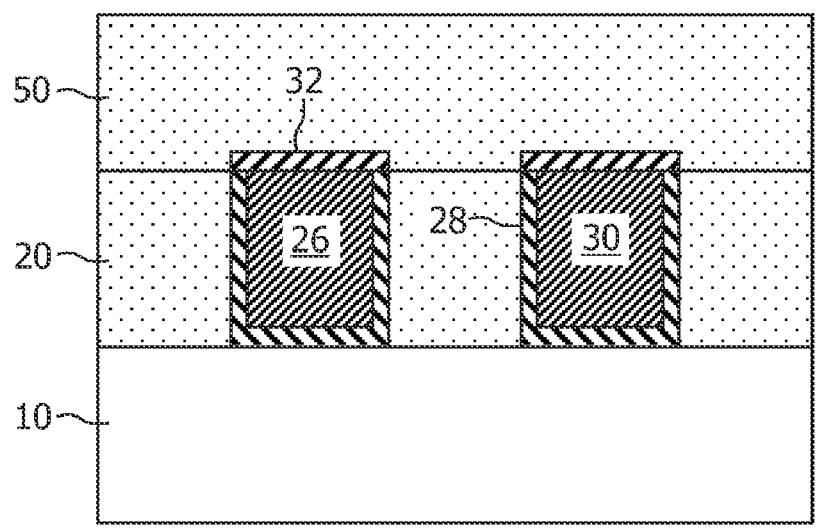
FIG. 8 shows a side section of an alternative embodiment of a moisture sensor.

FIG. 8 illustrates one alternative embodiment in which a further low-k dielectric layer 50 is deposited on top of the structure of FIG. 5.

Figure 9:
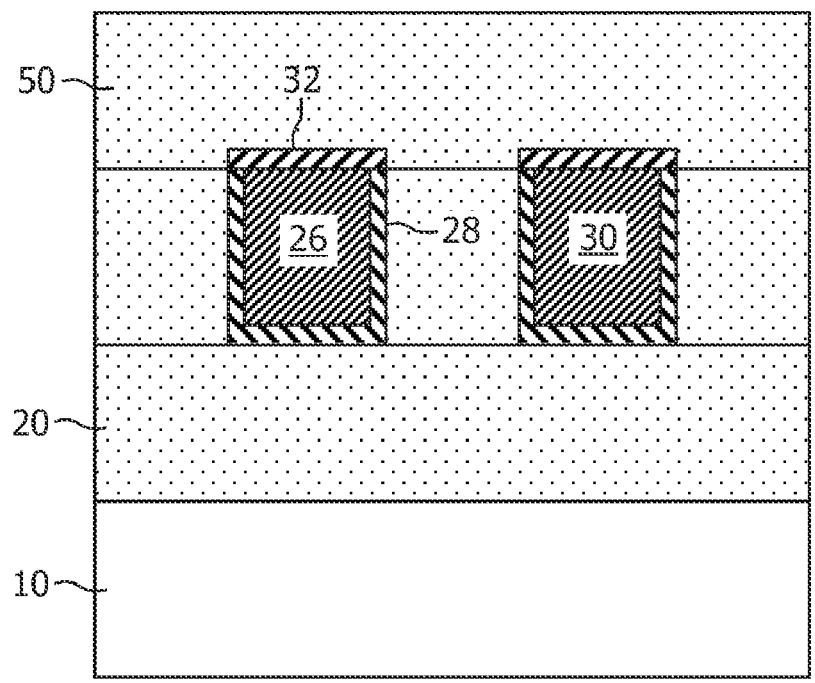
FIG. 9 shows a side section of an alternative embodiment of a moisture sensor.

A further alternative is illustrated in FIG. 9. This is made by forming a thicker low-k dielectric layer 20 and then etching trenches 26 not through the whole of this layer but only to a predetermined thickness.

This embodiment surrounds the electrodes 40, 42 with the porous low-k dielectric material.

Those skilled in the art will realise that many alternatives are possible for the details of the processing of these devices.

In particular, any suitable porous low-k dielectric or barrier material may be used. Aluminium electrodes may be used instead of copper.

The substrate may be a silicon substrate, or any alternative substrate such as an insulating substrate may also be used.

The moisture sensor can be formed as a single sensor on the substrate, or it may be integrated into an integrated circuit.

The invention claimed is;

1. A moisture sensor, comprising:
   first and second conductive electrodes each having at least one element, the elements of the first and second conductive electrodes extending in parallel with one another for a total parallel length of at least 0.3 mm and spaced apart by no more than 1 μm; and
   porous dielectric having a porosity greater than 10% separating the first and second electrodes.

2. A moisture sensor according to claim 1, wherein the first and second conductive electrodes are interdigitated combs, the teeth of the combs being the elements extending in total for the parallel length of at least 0.3 mm, the teeth of the first and second conductive elements being spaced from each other at the spacing of no more than 1 μm.

3. A moisture sensor according to claim 1, wherein the porous dielectric is of low-k dielectric orthosilicate glass having a dielectric constant less than 3.0.

4. A moisture sensor according to claim 1, further comprising a barrier layer extending around the conductive electrodes for protecting the conductive electrodes from corrosion.

5. A moisture sensor according to claim 4, wherein the barrier layer includes a first barrier material on the sides and base of the conductive electrodes and second barrier material on the top of the conductive electrodes, the first and second barrier materials being different.

6. A moisture sensor according to claim 5, wherein the second barrier material is a barrier material that can be selectively deposited on the conductive electrode material.

7. A moisture sensor according to claim 5, wherein the second barrier material is a dielectric barrier.

8. A moisture sensor according to claim 5, wherein the first barrier material is metal.

9. Use of a moisture sensor according to claim 5, comprising:
   applying an electric field from 0.5 to 1 MV/cm between the first and second electrodes, and
   measuring the current passing between the first and second electrodes as a measure of the moisture content.

10. A method of manufacturing a moisture sensor, comprising:
    depositing porous dielectric with a porosity of at least 10%;
    etching through the porous dielectric to form first and second trenches each having at least one element, the elements of the first and second trenches extending in parallel with one another for a total parallel length of at least 0.3 mm and being spaced apart by no more than 1 μm; and filling the trenches with conductor to form first and second conductive electrodes having elements extending in parallel for a total parallel length of at least 0.3 mm and spaced apart by no more than 1 μm.

11. A method according to claim 10, wherein the first and second trenches and first and second electrodes are interdigitated combs, the teeth of the combs extending in total for the parallel length of at least 0.3 mm and the teeth of each comb being between the teeth of the other comb at the spacing of no more than 1 μm.

12. A method according to claim 10, wherein the porous dielectric is a low-k dielectric with a dielectric constant less than 3.0.

13. A method according to claim 10, wherein the step of filling the trenches includes:

depositing a barrier layer of a first barrier material on the sidewalls and base of the trenches; and filling the trenches with a conductive filling material.

14. A method according to claim 13, further comprising depositing a second barrier material on the conductive filling material by selective deposition after filling the trenches with the conductive filling material to form a barrier layer extending around the top, sides and base of the conductive filling material.

15. A moisture sensor, comprising:

first and second conductive electrodes each having at least one element, the elements of the first and second conductive electrodes extending in parallel with one another for a total parallel length of at least 0.3 mm and spaced apart by no more than 1 μm;

porous dielectric having a porosity greater than 10% separating the first and second electrodes;

a corrosion protector, configured and arranged around the conductive electrodes from the corrosion, the corrosion protector and the porous dielectric being configured and arranged with the first and second conductive electrodes for passing current between the first and second conductive electrodes in response to an electric field from 0.5 to 1 MV/cm between the first and second electrodes; and moisture sufficiently present to increase the current by at least an order of magnitude in the presence of the moisture than without.

16. The moisture sensor according to claim 15 wherein the moisture is sufficiently present to increase the current by at least two orders of magnitude in the presence of the moisture than without.

17. The moisture sensor according to claim 15 wherein the barrier layer includes a first barrier material on the sides and base of the conductive electrodes and second barrier material on the top of the conductive electrodes, the first and second barrier materials being different.

18. The moisture sensor according to claim 15 wherein the barrier layer includes a first barrier material on the sides and base of the conductive electrodes and second barrier material on the top of the conductive electrodes, the first and second barrier materials being different; and the moisture is sufficiently present to increase the current by at least two orders of magnitude in the presence of the moisture than without.

* * * * *